United States Patent [19]
Curtis et al.

[11] Patent Number: 5,861,407
[45] Date of Patent: Jan. 19, 1999

[54] TETRAHYDROPYRIDINE DERIVATIVES AS DOPAMINE RECEPTOR SUBTYPE LIGANDS

[75] Inventors: Neil Roy Curtis, Puckeridge; Janusz Jozef Kulagowski, Sawbridgeworth; Paul David Leeson, Melbourne; Ian Michael Mawer, Bishops Stortford; Mark Peter Ridgill, Watton at Stone, all of England

[73] Assignee: Merck Sharp & Dohme, Ltd., Hoddesdon, United Kingdom

[21] Appl. No.: 803,906

[22] Filed: Feb. 21, 1997

[30] Foreign Application Priority Data

Feb. 26, 1996 [GB] United Kingdom .................. 9604036

[51] Int. Cl.$^6$ .................. A61K 31/44; A61K 31/435; C07D 211/70; C07D 491/056
[52] U.S. Cl. .................. 514/277; 514/302; 514/332; 514/333; 514/335; 514/336; 514/338; 514/339; 514/341; 514/343; 514/357; 546/2; 546/115; 546/255; 546/256; 546/261; 546/266; 546/268; 546/270; 546/271; 546/273; 546/278; 546/281; 546/283; 546/284; 546/286; 546/329
[58] Field of Search .................. 514/277, 302, 514/332, 333, 336, 335, 338, 339, 341, 343, 357; 546/255, 256, 261, 266, 268, 269, 270, 271, 273, 278, 281, 283, 284, 286, 329, 331, 2, 115

[56] References Cited

U.S. PATENT DOCUMENTS

| 3,965,102 | 6/1976 | Hauck et al. | 260/286 R |
| 4,169,200 | 9/1979 | Hauck et al. | 542/429 |
| 5,576,336 | 11/1996 | Baker et al. | 514/323 |

FOREIGN PATENT DOCUMENTS

| 2101997 | 8/1972 | Germany . |
| 2348951 | 4/1974 | Germany . |
| 29 04 451 | 8/1979 | Germany . |
| 2904451 | 8/1979 | Germany . |
| 9421615 | 9/1994 | WIPO . |
| 9421627 | 9/1994 | WIPO . |

*Primary Examiner*—Phyllis G. Spivack
*Attorney, Agent, or Firm*—Philippe L. Durette; Melvin Winokur

[57] ABSTRACT

A class of substituted 1,2,3,6-tetrahydropyridine derivatives are disclosed that are ligands for dopamine receptor subtypes within the body. These compounds are therefore useful in the treatment and/or prevention of disorders of the dopamine system, in particular schizophrenia or depression.

6 Claims, No Drawings

TETRAHYDROPYRIDINE DERIVATIVES AS DOPAMINE RECEPTOR SUBTYPE LIGANDS

This invention relates to the therapeutic use of a particular class of heterocyclic compounds. More particularly, the invention is concerned with the therapeutic use of substituted tetrahydropyridine derivatives which have been found to be ligands for dopamine receptor subtypes within the body, in particular the dopamine $D_4$ receptor subtype. These compounds are therefore of use in the treatment and/or prevention of disorders of the dopamine system, including schizophrenia, depression, anxiety, nausea, Parkinson's disease, tardive dyskinesias and extrapyramidal side-effects associated with treatment by conventional neuroleptic agents, neuroleptic malignant syndrome, disorders of hypothalamic-pituitary function such as hyperprolactinaemia and amenorrhoea, and delusional disorders (cf. Catalano et al., *Biol. Psychiatry*, 1993, 34, 459).

Upper gastrointestinal tract motility is believed to be under the control of the dopamine system. The compounds of use in the present invention may thus be of use in the prevention and/or treatment of gastrointestinal disorders, and the facilitation of gastric emptying.

Dependence-inducing agents such as cocaine and amphetamine have been shown to interact with the dopamine system. Compounds capable of counteracting this effect, including the compounds of use in the present invention, may accordingly be of value in the prevention or reduction of dependence on a dependence-inducing agent.

Dopamine is known to be a peripheral vasodilator; for example, it has been shown to exert a dilatory effect on the renal vascular bed. This implies that the compounds of use in the present invention may be beneficial in controlling vascular blood flow.

The localisation of dopamine receptor mRNA in rat heart and large vessels has been noted. This suggests a role for dopamine receptor ligands in controlling cardiovascular function, either by affecting cardiac and smooth muscle contractility or by modulating the secretion of vasoactive substances. The compounds of use in the present invention may therefore be of assistance in the prevention and/or treatment of such conditions as hypertension and congestive heart failure.

By virtue of their activity as ligands for dopamine receptor subtypes within the body, the compounds of use in the present invention may also be of benefit in enhancing cognitive function, and in treating and/or preventing cognitive disorders including presenile and senile dementia (also known as Alzheimer's disease and senile dementia of the Alzheimer type respectively).

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., *Nature (London)*, 1991, 350, 610) and $D_5$ (Sunahara et al., *Nature (London)*, 1991, 350, 614) receptor subtypes have been described.

In U.S. Pats. 3,965,102 and 4,169,200, and in DE-A -2904451, are described, as intermediates, various substituted tetrahydropyridine derivatives. In none of these publications, however, is there any suggestion of therapeutic utility for the relevant tetrahydropyridine derivatives described therein.

The compounds of use in the present invention, being ligands for dopamine receptor subtypes within the body, in particular the $D_4$ receptor subtype, are accordingly of use in the treatment and/or prevention of disorders of the dopamine system, including schizophrenia and depression.

The present invention provides a pharmaceutical composition comprising a compound of formula I, or a pharmaceutically acceptable salt thereof:

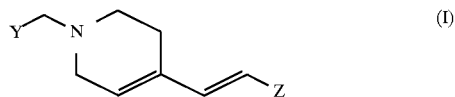

wherein

Y and Z independently represent a group of formula (a), (b), (c) or (d):

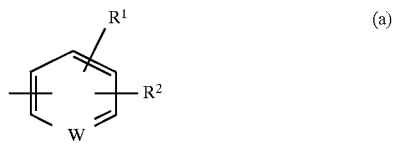

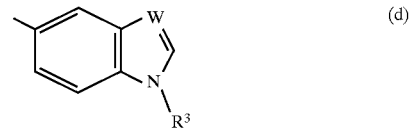

in which

W represents CH or nitrogen;

X represents oxygen, sulphur or N-R3;

$R^1$ and $R^2$ independently represent hydrogen, halogen, cyano, nitro, trifluoromethyl, $C_{1-6}$ alkyl, $C_{1-6}$ alkoxy or $C_{1-6}$, alkylsulphonyl; or $R^1$ and $R^2$, when situated on adjacent carbon atoms, together represent methylenedioxy; and $R^3$ represents hydrogen or $C_{1-6}$ alkyl; in association with a pharmaceutically acceptable carrier.

The present invention also provides a compound of formula I as defined above or a pharmaceutically acceptable salt thereof for use in therapy.

In another aspect, the present invention provides the use of a compound of formula I as defined above or a pharmaceutically acceptable salt thereof for the manufacture of a medicament for the prevention and/or treatment of clinical conditions for which a dopamine receptor subtype ligand, in particular a selective ligand for the dopamine $D_4$ receptor subtype, is indicated.

In a further aspect, this invention provides a method for the prevention and/or treatment of clinical conditions for which a dopamine receptor subtype ligand, in particular a selective ligand for the dopamine $D_4$ receptor subtype, is indicated, which method comprises administering to a patient in need of such treatment an effective amount of a compound of formula I as defined above or a pharmaceutically acceptable salt thereof As used herein, the expression "$C_{1-6}$ alkyl" relates to methyl and ethyl groups, and straight-chained or branched propyl, butyl, pentyl and hexyl groups. Particular alkyl groups include methyl, ethyl, n-propyl, isopropyl and tert-butyl. Derived expressions such as "$C_{1-6}$ alkoxy" and "$C_{1-6}$ alkylsulphonyl" are to be construed accordingly.

The term "halogen" as used herein includes fluorine, chlorine, bromine and iodine, especially fluorine or chlorine.

Where the compounds of use in the invention have at least one asymmetric centre, they may accordingly exist as enantiomers. Where the compounds of use in the invention possess two or more asymmetric centres, they may additionally exist as diastereoisomers. It is to be understood that the use of all such isomers and mixtures thereof in any proportion is encompassed within the scope of the present invention.

For use in medicine, the salts of the compounds of formula I will be pharmaceutically acceptable salts. Other salts may, however, be useful in the preparation of the compounds of use in the invention or of their pharmaceutically acceptable salts. Suitable pharmaceutically acceptable salts of the compounds of use in this invention include acid addition salts which may, for example, be formed by mixing a solution of the compound of use in the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

Suitably, the moiety Y in formula I above represents a group of formula (a), (c) or (d) as defined above.

Suitably, Z represents a group of formula (a), (b) or (d) as defined above.

Suitably, X is sulphur.

Suitable values for the group $R^1$ include hydrogen, fluoro, chloro, iodo, cyano, nitro, trifluoromethyl, methyl, methoxy and methylsulphonyl.

Suitably, $R^2$ represents hydrogen, fluoro or chloro.

Alternatively, $R^1$ and $R^2$, when situated on adjacent carbon atoms, may together represent methylenedioxy.

Suitably, $R^3$ represents hydrogen or methyl.

Particular values for the substituent Y in the compounds of formula I above include phenyl, 4-fluorophenyl, 4-chlorophenyl, 4-iodophenyl, 3,4-dichlorophenyl, 4-cyanophenyl, 4-nitrophenyl, 4-trifluoromethylphenyl, 4-methylphenyl, 3-methoxyphenyl, 4- methoxyphenyl, indol-5-yl, benzimidazol-5-yl and imidazol-4-yl.

Particular values for the substituent Z include phenyl, 2-fluorophenyl, 4-fluorophenyl, 3-chlorophenyl, 4-chlorophenyl, 3,4-difluorophenyl, 3,5-difluorophenyl, 4-cyanophenyl, 4-methylphenyl, 3-methoxyphenyl, 3-fluoro-4-methoxyphenyl, 3-methanesulphonylphenyl, 3,4-methylenedioxyphenyl, 2-chloropyridin-5-yl, 2-thienyl, 3-thienyl, indol -5-yl and 1-methylindol-5-yl.

A particular compound of use in the pharmaceutical formulations and therapeutic methods of the present invention is (E)-1-benzyl-4-(2-phenylethenyl)-1,2,3,6-tetrahydropyridine; and pharmaceutically acceptable salts thereof.

Certain specific compounds falling within the scope of formula I above are novel. In a still further aspect, therefore, the invention provides a compound selected from the following:

(E)-1-benzyl-4-[2-(3-methoxyphenyl)ethenyl]-1,2,3,6-tetrahydropyridine;
(E)-1-benzyl-4-[2-(4-chlorophenyl)ethenyl]-1,2,3,6-tetrahydropyridine; (E)-1-benzyl-4-[2-(3,4-difluorophenyl)ethenyl]-1,2,3,6-tetrahydropyridine;
(E)-1-benzyl-4-[2-(3,5-difluorophenyl)ethenyl]-1,2,3,6-tetrahydropyridine;
(E)-1-benzyl-4-[2-(2-fluorophenyl)ethenyl]-1,2,3,6-tetrahydropyridine;
(E)-1-benzyl-4-[2-(thien-3-yl)ethenyl]-1,2,3,6-tetrahydropyridine;
(E)-1-benzyl-4-[2-(thien-2-yl)ethenyl]-1,2,3,6-tetrahydropyridine;
(E)-4-[2-(4-cyanophenyl)ethenyl] -1-(4-methoxybenzyl)-1,2,3,6-tetrahydropyridine;
(E)-1-(4-chlorobenzyl)-4-[2-(4-methylphenyl)ethenyl]-1,2,3,6-tetrahydropyridine;
(E)-1-(4-chlorobenzyl)-4-[2-(3,4-methylenedioxyphenyl)ethenyl]-1,2,3,6-tetrahydropyridine;
(E)-1-(4-methylbenzyl)-4-[2-(3,4-methylenedioxyphenyl)ethenyl]-1,2,3,6-tetrahydropyridine;
(E)-1-(4-chlorobenzyl)-4-[2-(thien-3-yl)ethenyl]-1,2,3,6-tetrahydropyridine;
(E)-4-[2-(4-fluorophenyl)ethenyl]-1-(4-methylbenzyl)-1,2,3,6-tetrahydropyridine;
(E)-1-(4-cyanobenzyl)-4-[2-(4-fluorophenyl)ethenyl]-1,2,3,6-tetrahydropyridine;
(E)-1-(3-methoxybenzyl)-4-(2-phenylethenyl)-1,2,3,6-tetrahydropyridine;
(E)-1-benzyl-4-[2-(indol-5-yl)ethenyl]-1,2,3,6-tetrahydropyridine;
(E)-1-(4-chlorobenzyl)-4-[2-(indol-5-yl)ethenyl]-1,2,3,6-tetrahydropyridine;
(E)-1-benzyl-4-[2-(2-chloropyridin-5-yl)ethenyl]-1,2,3,6-tetrahydropyridine;
(E)-1-benzyl-4-[2-(1-methylindol-5-yl)ethenyl]-1,2,3,6-tetrahydropyridine;
(E)-1-benzyl-4-[2-(3-fluoro-4-methoxy)phenylethenyl]-1,2,3,6-tetrahydropyridine;
(E)-1-(4-methoxybenzyl)-4-(2-phenylethenyl)-1,2,3,6-tetrahydropyridine;
(E)-1-(4-chlorobenzyl)-4-(2-phenylethenyl)-1,2,3,6-tetrahydropyridine;
(E)-1-(4-fluorobenzyl)-4-(2-phenylethenyl)-1,2,3,6-tetrahydropyridine;
(E)-1-(4-chlorobenzyl)-4-[2-(4-chlorophenyl)ethenyl]-1,2,3,6-tetrahydropyridine;
(E)-1-benzyl-4-[2-(3-methanesulphonylphenyl)ethenyl]-1,2,3,6-tetrahydropyridine;
(E)-1-(3,4-dichlorobenzyl)-4-(2-phenylethenyl)-1,2,3,6-tetrahydropyridine;
(E)-1-(4-methylbenzyl)-4-(2-phenylethenyl)-1,2,3,6-tetrahydropyridine;
(E)-1-(4-cyanobenzyl)-4-(2-phenylethenyl)-1,2,3,6-tetrahydropyridine;
(E)-1-(4-chlorobenzyl)-4-[2-(3-chlorophenyl)ethenyl]-1,2,3,6-tetrahydropyridine;
(E)-1-(4-nitrobenzyl)-4-(2-phenylethenyl)-1,2,3,6-tetrahydropyridine;
(E)-4-[2-(3-chlorophenyl)ethenyl]-1-(4-methylbenzyl)-1,2,3,6-tetrahydropyridine;
(E)-1-(4-iodobenzyl)-4-(2-phenylethenyl)-1,2,3,6-tetrahydropyridine;
(E)-4-(2-phenylethenyl)-1-(4-trifluoromethylbenzyl-1,2,3,6-tetrahydropyridine;
(E)-4-[2-(4-chlorophenyl)ethenyl]-1-(4-methylbenzyl)-1,2,3,6-tetrahydropyridine;
(E)-1-(indol-5-yl)methyl-4-(2-phenylethenyl)-1,2,3,6-tetrahydropyridine;
(E)-5-[4-(2-phenylethenyl)-1,2,3,6-tetrahydropyridin-1-yl]methyl -benzimidazole;
(E)-4-[4-(2-phenylethenyl)-1,2,3,6-tetrahydropyridin-1-yl]methyl-imidazole;
and pharmaceutically acceptable salts thereof.

The invention also provides pharmaceutical compositions comprising one or more of the novel compounds of this invention in association with a pharmaceutically acceptable carrier.

The compositions in accordance with the present invention are suitably in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Favoured unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia or depression, a suitable dosage level is about 0.001 to 250 mg/kg per day, preferably about 0.005 to 100 mg/kg per day, and especially about 0.01 to 5 mg/kg per day. The compounds may be administered on a regimen of 1 to 4 times per day.

In order to alleviate the symptoms of schizophrenia without causing sedation or extrapyramidal side-effects, it is believed that the dosage level of the active ingredient should be selected such that the dose administered is effective in substantially completely blocking the dopamine $D_4$ receptor subtype in human brain whilst displaying no or negligible $D_2$ receptor subtype occupancy. A suitable dosage level in this regard is about 0.001 to 5.0 mg/kg per day, more particularly about 0.005 to 1.0 mg/kg per day, and especially about 0.01 to 0.5 mg/kg per day.

If desired, the compounds of use in this invention may be co-administered with another medicament, for example a known anti-schizophrenic agent which produces its effects via dopamine $D_2$ and/or $5\text{-}HT_2$ receptor blockade. Such co-administration may be desirable where a patient is already on an established treatment regime, for example one involving conventional anti-schizophrenic medicaments such as haloperidol or chlorpromazine.

The compounds of formula I above, including the novel compounds according to the invention, may be prepared by a process which comprises reacting a compound of formula II with a compound of formula III:

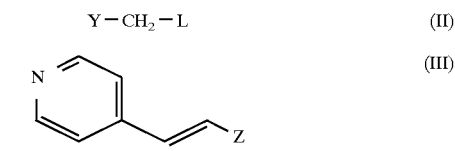

wherein Y and Z are as defined above, and L represents a suitable leaving group; followed by treatment of the resulting pyridinium salt with a reducing agent.

The leaving group L is suitably a halogen atom, e.g. chlorine or bromine; or a $C_{1-6}$ alkylsulphonyloxy group, e.g. methanesulphonyloxy (mesyloxy).

Where L represents a halogen atom, the reaction between compounds II and III is conveniently effected in a suitable solvent, e.g. N,N-dimethylformamide, typically at an elevated temperature.

Reduction of the pyridinium salt is conveniently brought about by treatment with a reducing agent such as sodium borohydride, typically in a lower alkanol such as ethanol.

In an alternative procedure, the compounds of formula I above, including the novel compounds according to the invention, may be prepared by a process which comprises reducing a compound of formula IV:

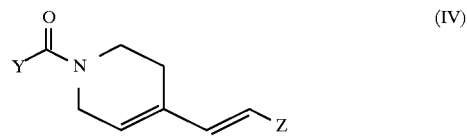

wherein Y and Z are as defined above.

The reduction is conveniently effected by treating compound IV with a reducing agent such as lithium aluminium hydride in an appropriate solvent, e.g. diethyl et her, tetrahydrofuran or 1,2-dimethoxyethane, or mixtures thereof.

The compounds of formula IV above may suitably b e prepared by reacting a compound of formula V with the appropriate compound of formula VI:

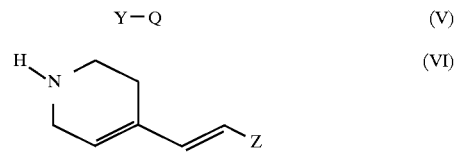

wherein Y and Z are as defined above, and Q represents a reactive carboxylate moiety.

Suitable values for the reactive carboxylate moiety Q include esters, for example $C_{1-4}$ alkyl esters; acid anhydrides, for example mixed anhydrides with $C_{1-4}$ alkanoic acids; acid halides, for example acid chlorides; and acylimidazoles.

By way of example, the intermediates of formula V above wherein Q istermdiad chloride moiety may be prepared by treating the corresponding carboxylic acid derivative with thionyl chloride. Similarly, the intermediates of formula V wherein Q is an acylimidazole moiety may be prepared by treating the corresponding carboxylic acid derivative with 1,1'-carbonyldiimidazole. Alternatively, the reactive carboxylate moiety Q may be obtained by treating the corresponding compound wherein Q is carboxy with 1-(3-dimethylaminopropyl)-3-ethylcarbodlumide hydrochloride and 1-hydroxybenzotriazole hydrate, optionally in the presence of triethylamine; the resulting activated carboxylate intermediate may then suitably be reacted in situ with the required compound of formula VI.

The intermediates of formula VI above may be prepared by deprotection of a compound of formula VII:

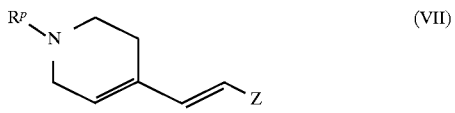

wherein Z is as defined above, and RP represents an amino-protecting group.

The amino-protecting group RP is suitably benzyl, which can conveniently be removed as necessary by treating compound VII with 1-chloroethyl chloroformate in a solvent such as dichloromethane, followed by heating under reflux in methanol.

In another procedure, the compounds of formula I above, including the novel compounds in accordance with the invention, may be prepared by a process which comprises reacting a compound of formula II as defined above with a compound of formula VI as defined above.

The reaction is conveniently carried out under basic conditions in a suitable solvent, e.g. potassium carbonate in N,N-dimethylformamide.

Where they are not commercially available, the starting materials of formula II, III, V and VII may be prepared by methods analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art. Indeed, as will be appreciated, the compounds of formula VII wherein RP is benzyl are compounds of use in the invention in their own right.

Where the above-described processes for the preparation of the compounds of use in the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (-)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Orgaitic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds of use in the invention.

The compounds useful in this invention potently inhibit [$^3$H]-spiperone binding to human dopamine $D_4$ receptor subtypes expressed in clonal cell lines.

[$^3$H]-Spiperone Binding Studies

Clonal cell lines expressing the human dopamine $D_4$ receptor subtype were harvested in PBS and then lysed in 10 mM Tris-HCl pH 7.4 buffer containing 5 mM $MgSO_4$ for 20 min on ice. Membranes were centrifuged at 50,000 g for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–100 μg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 μM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and were found to possess a Ki value for displacement of [3H]-spiperone from the human dopamine $D_4$ receptor subtype of below 1.5 μM in each case.

EXAMPLE 1

(E)-1-Benzyl-4-(2-phenylethenyl)-1,2,3,6-tetrahydropyridine hydrochloride

Step 1: (E)-4-(2-Phenylethenyl)pyridine

A solution of 4-picoline (18.6 g, 0.2 mol) and benzaldehyde (21.2 g, 0.2mol) in acetic anhydride (125 ml) was stirred under reflux for 24 h. The resulting black solution was evaporated, the residue partitioned between ethyl acetate (100 ml) and aqueous sodium carbonate (100 ml) and the liquid phases decanted from the solid residue. The organic layer was washed with sodium carbonate (100 ml), dried ($MgSO_4$), and evaporated to leave a black solid. The solid remaining from the earlier extraction was dissolved in dichloromethane (100 ml), the solution washed with sodium carbonate (75 ml), dried ($MgSO_4$) and evaporated. The combined solid residues were dissolved in methanol (200 ml), treated with charcoal, filtered and the filtrate evaporated to leave a brown solid which was triturated with cyclohexane, the suspension filtered and the solid recrystallised from cyclohexane to leave the product as a brown crystalline powder (11.94 g). The combined organic supernatants were chromatographed on silica gel eluting with ethyl acetate/hexanes (7:3) to give a further crop as a yellow solid (6.2 g).

Step 2: (E)-1-Benzyl-4-(2-phenylethenyl)-1,2,3,6-tetrahydropyridine hydrochloride A solution of the foregoing pyridine (4.16 g, 23 mmol) and benzyl bromide (3.0 ml, 25 mmol) in DMF (15 ml) was stirred at 100° C. for 1 h to give a thick paste, which was allowed to cool before being diluted with ethanol (100 ml). Sodium borohydride (1.12 g, 29.5 mmol) was added in portions to the stirred suspension, and the mixture stirred for 2 h at room temperature, and then at reflux for 1 h. On cooling, the solvent was removed and the residue partitioned between water (100 ml) and ethyl acetate (3×50 ml), the organic layers dried (MgSO$_4$) and evaporated. The residue was subjected to chromatography on silica gel, eluting with ethyl acetate in hexanes (20%), to give the product as a yellow solid (3.46 g). Conversion to the hydrochloride and recrystallisation from methanol gave the title compound as a buff solid, m.p. 230° C. (dec); (Found: C, 76.71; H, 6.89; N, 4.29. C$_{20}$H$_{22}$ClN requires C, 77.03; H, 7.11; N, 4.49%); $\delta_H$(DMSO-d$_6$) 2.56–2.79 (2H, m, tetrahydropyridinyl CH$_2$), 3.11–3.23 (1H, m, tetrahydropyridinyl CH$_2$), 3.50–3.83 (3H, m, tetrahydropyridinyl CH$_2$), 4.35–4.40 (2H, m, ArCH$_2$N), 5.88 (1H, br s, —CH=CR—), 6.61 (1H, d, J 16.3 Hz, —CH=CHPh), 6.97 (1H, d, J 16.3 Hz, —CH=CHPh), 7.25 (1H, t, J 7.3 Hz, ArH), 7.35 (2H, t, J 7.3 Hz, ArH), 7.47–7.52 (5H, m, ArH), 7.65–7.66 (2H, m, ArH), and 11.05 (1H, br s, NH$^+$); m/z (CI$^+$, NH$_3$) 276 (M+1)$^+$.

Prepared analogously were:

EXAMPLE 2
(E)-1-Benzyl-4-(2-[3-methoxyphenyl]ethenyl)-1,2,3,6-tetrahydropyridine hydrochloride M.p. 218°–220° C. (MeOH/Et$_2$O); (Found: C, 73.57; H, 7.01; N, 4.04. C$_{21}$H$_{24}$ClNO requires C, 73.78; H, 7.08; N, 4.10%); $\delta_H$(DMSO-d$_6$) 2.64–2.70 (2H, m, tetrahydropyridinyl CH$_2$), 3.16 (1H, br s, tetrahydropyridinyl CH$_2$), 3.57 (1H, br s, tetrahydropyridinyl CH$_2$), 3.69–3.79 (2H, m, tetrahydropyridinyl CH$_2$), 3.77 (3H, s, OMe), 4.35–4.40 (2H, m, ArCH$_2$N), 5.88 (1H, br s, —CH=CR—), 6.58 (1H, d, J 16.3 Hz, —CH=CH—), 6.83 (1H, dd, J 8.5, 2.1 Hz, ArH), 6.98 (1H, d, J 16.3 Hz, —CH=CH—), 7.07–7.09 (2H, m, ArH), 7.26 (1H, t, J 8.1 Hz, ArH), 7.46–7.48 (3H, m, ArH), 7.66–7.67 (2H, m, ArH), and 11.15 (1H, br s, NH$^+$); m/z (CI$^+$, NH$_3$) 306 (M+1)$^+$.

EXAMPLE 3
(E)-1-Benzyl-4-(2-[4-chlorophenyl]ethenyl)-1,2,3,6-tetrahydropyridine M.p. 123°–125° C. (60°–80° petrol); (Found: C, 77.36; H, 6.51; N, 4.44. C$_{20}$H$_{20}$ClN requires C, 77.53; H, 6.51; N, 4.52%); $\delta_H$ (CDCl$_3$) 2.40 (2H, br s, tetrahydropyridinyl CH$_2$), 2.67 (2H, t, J 5.8 Hz, tetrahydropyridinyl CH$_2$), 3.14 (2H, d, J 2.6 Hz, tetrahydropyridinyl CH$_2$), 3.62 (2H, s, ArCH$_2$N), 5.83 (1H, br s, —CH=CR—), 6.38 (1H, d, J 16.1 Hz, —CH=CH—), 6.74 (1H, d, J 16.1 Hz, —CH=CH—), and 7.24–7.38 (9H, m, ArH); m/z (CI$^+$, NH$_3$) 310 (M+1)$^+$.

EXAMPLE 4
(E)-1-Benzyl-4-(2-[3,4-difluorophenyl]ethenyl)-1,2,3,6-tetrahydropyridine hydrochloride hemihydrate M.p. 215° C. (dec.) (MeOH/Et$_2$O); (Found: C, 67.63; H, 5.85; N, 3.91. C$_{20}$H$_{20}$ClF$_2$N.0.5H$_2$O requires C, 67.32; H, 5.93; N, 3.93%); $\delta_H$ (DMSO-d$_6$) 2.61 (2H, m, tetrahydropyridinyl CH$_2$), 3.15 (1H, br s, tetrahydropyridinyl CH$_2$), 3.58 (1H, m, tetrahydropyridinyl CH$_2$), 3.69 (2H, br s, tetrahydropyridinyl CH$_2$), 4.35 (2H, m, ArCH$_2$N), 5.89 (1H, br s, —CH=CR—), 6.59 (1H, d, J 16.2 Hz, —CH=CH—), 6.99 (1H, d, J 16.2 Hz, —CH=CH—), 7.35–7.46 (5H, m, ArH), 7.64–7.67 (3H, m, ArH), and 11.01 (1H, br s, NH$^+$); m/z (CI$^+$, NH$_3$) 312 (M+1)$^+$.

EXAMPLE 5
(E)-1-Benzyl-4-[2-(3, 5-difluorophenyl)ethenyl]-1,2,3,6-tetrahydropyridine hydrogen oxalate M.p. 248°–250° C. (MeOH); (Found: C, 65.53; H, 5.25; N, 3.32. C$_{20}$H$_{19}$F$_2$N.(CO$_2$H)$_2$ requires C, 65.83; H, 5.27; N, 3.49%); $\delta^H$-1 (DMSO-d$_6$) 2.49–2.51 (2H, m, tetrahydropyridinyl CH$_2$), 3.08 (2H, m, tetrahydropyridinyl CH$_2$), 3.49 (2H, m, tetrahydropyridinyl CH$_2$), 4.07 (2H, s, ArCH$_2$N), 5.96 (1H, s, —CH=CR—), 6.56 (1H, d, J 16.2 Hz, —CH=CH—), 7.05–7.14 (2H, m, —CH=CH— and ArH), 7.26 (2H, dd, J 9.1, 2.1 Hz, ArH), and 7.41–7.45 (5H, m, ArH); m/z (ES$^+$) 312 (M+1)$^+$.

EXAMPLE 6
(E)-1-Benzyl-4-(2-(2-fluoro)phenylethenyl)-1,2,3,6-tetrahydropyridine hydrogen oxalate M.p. 224°–226° C. (dec.) (MeOH); (Found: C, 68.13; H. 5.62; N, 3.53. C$_{22}$H$_{22}$FNO$_4$.0.25H$_2$O requires C, 68.12; H, 5.85; N, 3.61%); $\delta_H$ (DMSO-d$_6$) 2.53 (2H, br s, tetrahydropyridinyl CH$_2$), 3.10 (2H, m, tetrahydropyridinyl CH$_2$), 3.51 (2H, br s, tetrahydropyridinyl CH$_2$), 4.10 (2H, s, PhCH$_2$N), 5.95 (1H, br s, —CH=R—), 6.61 (1H, d, J 16.4 Hz, CH=CHAr), 7.03 (1H, (1, J 16.4 Hz, CH=CHAr), 7.19 (2H, m, ArH), 7.30 (1H, m, ArH), 7.39–7.48 (5H, m, ArH), and 7.68 (1H, m, ArH); m/z (ES$^+$) 294 (M+1)$^+$.

EXAMPLE 7
(E)-1-Benzyl-4-[2-(thien-3-yl)ethenyl]-1,2,3,6-tetrahydropyridine hydrochloride M.p. 225°–227° C. (MeOH/Et$_2$O); (Found: C, 66.26; H, 6.41; N, 4.23. C$_{18}$H$_{19}$NS, HCl, 0.5H$_2$O requires C, 66.14; H, 6.47; N, 4.28%); $\delta_H$ (DMSO -d$_6$) 2.52–2.66 (2H, m, tetrahydropyridinyl CH$_2$), 3.11 (2H, br s, tetrahydropyridinyl CH$_2$), 3.69 (2H, br s, tetrahydropyridinyl CH$_2$), 4.33 (2H, br s, PhCH$_2$N), 5.80 (1H, br s, tetrahydropyridinyl 5-CH), 6.63 (1H, d, J 16.3 Hz, ArCH=CHC), 6.75 (1H, d, J 16.3 Hz, ArCH=CHC), 7.32–7.34 (1H, m, ArH), 7.43–7.49 (5H, m, ArH), 7.64–7.67 (2H, m, ArH); m/z (CI$^+$, NH$_3$) 282 (M+1)$^+$.

EXAMPLE 8
(E)-1-Benzyl-4-[2-(thien-2-yl)ethenyl]-1,2,3,6-tetrahydropyridine hydrochloride M.p. 220°–225° C. (MeOH/Et$_2$O); (Found: C, 64.40; H, 6.70; N, 4.27. C$_{18}$H$_{19}$NS.HCl.H$_2$O requires C, 64.36; H, 6.60; N, 4.17%); 6,f (DMSO-d$_6$) 2.59–2.63 (2H, m, tetrahydropyridinyl CH$_2$), 3.17–3.20 (1H, m, tetrahydropyridinyl CH), 3.51–3.55 (1H, m, tetrahydropyridinyl CH), 3.66–3.70 (2H, m, tetrahydropyridinyl CH$_2$), 4.34–4.38 (2H, br s, PhCH$_2$N), 5.86 (1H, br s, tetrahydropyridinyl 5-CH), 6.66 (1H, d, J 16.1 Hz, ArCH=CHC), 6.81 (1H, d, J 16.1 Hz, ArCH=CHC), 7.02–7.05 (1H, m, ArH), 7.15–7.17 (1H, m, ArH), 7.44–7.48 (4H, m, ArH), and 7.62–7.64 (2H, m, ArH); m/z (CI$^+$, NH$_3$) 282 (M+1)$^+$.

EXAMPLE 9
(E)-4-[2-(4-Cyanophenyl)ethenyl]-1-(4-methoxybenzyl)-1,2,3,6-tetrahydropyridine M.p. 120°–121° C. (MeOH); (Found: C, 79.96; H, 6.54; N, 8.41. C$_{22}$H$_{22}$NO requires C, 79.97; H, 6.71; N, 8.48%); $\delta_H$ (CDCl$_3$) 2.40 (2H, br s, tetrahydropyridinyl CH$_2$), 2.66 (2H, t, J 5.8 Hz, tetrahydropyridinyl CH$_2$), 3.13 (2H, br s, tetrahydropyridinyl CH$_2$), 3.56 (2H, br s, ArCH$_2$N), 3.81 (3H, s, OCH$_3$), 5.92 (1H, br s, tetrahydropyridinyl 5-CH), 6.40 (1H, d, J 16.1 Hz, ArCH=CHC), 6.85–6.89 (3H, m, ArCH=CHC), 7.27 (2H, d, J 7.9 Hz, ArH), 7.45 (2H, d, J 8.4 Hz, ArH), and 7.57 (2H, d, ArH); m/z (ES$^+$) 331 (M+1)$^+$.

EXAMPLE 10
(E)-1-(4-Chlorobenzyl)-4-[2-(4-methylphenyl)ethenyl]-1,2,3,6-tetrahydropyridine M.p. 122°–124° C. (MeOH); (Found: C, 77.86; H, 6.88; N, 4.33. C$_{21}$H$_{22}$ClN requires C, 77.88; H, 6.85; N, 4.32%);

$\delta_H$ (CDCl$_3$) 2.33 (3H, s, ArCH$_3$), 2.41 (2H, br s, tetrahydropyridinyl CH$_2$), 2.65 (2H, t, J 8.1 Hz, tetrahydropyridinyl CH$_2$), 3.11 (2H, br s, tetrahydropyridinyl CH$_2$), 3.57 (2H, s, ArCH$_2$N), 5.78 (1H, br s, tetrahydropyridinyl 5-CH), 6.42 (1H, d, J 16.2 Hz, ArCH=CHC), 6.74 (1H, d, J 16.2 Hz, ArCH=CHC), 7.11 (2H, d, J 11.5 Hz, ArH), and 7.25–7.31 (6H, m, ArH); m/z (ES$^+$) 324 (M+1)$^+$.

EXAMPLE 11

(E)-1-(4-Chlorobenzyl)-4-[2-(3,4-methylenedioxyphenyl) ethenyl]-1,2,3,6-tetrahydropyridine M.p. 122°–124° C. (MeOH); (Found: C, 71.25; H, 5.51; N, 3.99. C$_{21}$H$_{20}$ClNO$_2$ requires C, 71.28; H, 5.69; N, 3.95%); $\delta_H$ (CDCl$_3$) 2.38 (3H, br s, tetrahydropyridinyl CH$_2$), 2.64 (2H, t, J 5.8 Hz, tetrahydropyridinyl CH$_2$), 3.11 (2H, br s, tetrahydropyridinyl CH$_2$), 3.57 (2H, s, ArCH$_2$N), 5.76 (1H, br s, tetrahydropyridinyl 5-CH), 5.94 (2H, s, OCH$_2$O), 6.36 (1H, d, J 16.1 Hz, ArCH=CHC), 6.62 (1H, d, J 16.1 Hz, ArCH=CHC), 6.74 (1H, d, J 8.1 Hz, 5-H), 6.81 (1H, d, J 8.1 Hz, 6-H), 6.94 (1H, s, 2-H), and 7.29 (4H, s, 2'-H, 3'-H, 5'-H, 6'-H); m/z (ES$^+$) 354 (M+1)$^+$.

EXAMPLE 12

(E)-1-(4-Methylbenzyl)-4-[2-(3,4-methylenedioxyphenyl) ethenyl]-1,2,3,6-tetrahydropyridine M.p. 128°–130° C. (MeOH); (Found: C, 79.02; H, 6.77; N, 4.14. C$_{22}$H$_{22}$NO$_2$ requires C, 79.25; H, 6.95; N, 4.20%); $\delta_H$ (CDCl$_3$) 2.34 (3H, s, ArCH$_3$), 2.38 (2H, br s, tetrahydropyridinyl CH$_2$), 2.65 (2H, t, J 5.7 Hz, tetrahydropyridinyl CH$_2$), 3.16 (2H, br s, tetrahydropyridinyl CH$_2$), 3.58 (2H, s, ArCH$_2$N), 5.76 (1H, br s, tetrahydropyridinyl 5-CH), 5.94 (2H, s, OCH$_2$O), 6.35 (1H, d, J 16.1 Hz, ArCH=CHC), 6.62 (1H, d, J 16.1 Hz, ArCH=CHC), 6.74 (1H, d, J 8.0 Hz, ArH), 6.81 (1H, d, J 8.4 Hz, ArH), 6.94 (1H, s, ArH), 7.13 (2H, d, J 8.0 Hz, ArH), and 7.24 (2H, d, J 8.0 Hz, ArH); m/z (ES$^+$) 334 (M+1)$^+$.

EXAMPLE 13

(E)-1-(4-Chlorobenzyl)-4-[2-(thien-3-yl)ethenyl]-1,2.3,6-tetrahydropyridine

M.p. 125°–127° C. (MeOH); (Found: C, 68.37: H, 5.66; N, 4.40. CH$_{18}$ClNS requires C, 68.25; H, 5.74; N, 4.43%); $\delta_H$ (CDCl$_3$) 2.38 (2H, br s, tetrahydropyridinyl CH$_2$), 2.65 (2H, t, J 5.8 Hz, tetrahydropyridinyl CH$_2$), 3.11 (2H, br s, tetrahydropyridinyl CH$_2$), 3.58 (2H, s, ArCH$_2$N), 5.76 (1H, br s, tetrahydropyridinyl 5-CH), 6.46 (1H, d, J 16.1 Hz, ArCH=CHC), 6.63 (1H, d, J 16.1 Hz, ArCH=CHC), 7.13 (1H, br s, ArH), and 7.21–7.37 (6H, m, ArH); m/z (ES$^+$) 316 (M+1)$^+$.

EXAMPLE 14

(E)-4-[2-(4-Fluorophenyl)ethenyl]-1-(4-methylbenzyl)-1,2,3,6-tetrahydropyridine

M.p. 111°–113° C. (MeOH); (Found: C, 81.74; H, 6.97; N, 4.52. C$_{21}$H$_{22}$FN requires C, 82.04; H, 7.21; N, 4.55%); $\delta_H$ (CDCl$_3$) 2.35 (3H, s, ArCH$_3$), 2.41 (2H, br s, tetrahydropyridinyl CH$_2$), 2.68 (2H, br s, tetrahydropyridinyl CH$_2$), 3.14 (2H, br s, tetrahydropyridinyl CH$_2$), 3.61 (2H, s, ArCH$_2$N), 5.79 (1H, br s, tetrahydropyridinyl 5-CH), 6.40 (1H, d, J 16.2 Hz, ArCH=CHC), 6.69 (1H, d, J 16.2 Hz, ArCH=CHC), 6.98 (2H, d, J 8.7 Hz, ArH), 7.14 (2H, d, J 7.8 Hz, ArH), 7.24–7.27 (2H, m, ArH), and 7.32–7.36 (2H, m, ArH); m/z (ES$^+$) 308 (M+1)$^+$.

EXAMPLE 15

(E)-1-(4-Cyanobenzyl)-4-[2-(4-fluorophenyl)ethenyl]-1,2,3,6-tetrahydropyridine

M.p. 150°–152° C. (MeOH); (Found: C, 79.32; H, 5.88; N, 8.69. C$_2$H$_{19}$FN$_2$ requires C, 79.21; H, 6.01; N, 8.80%); $\delta_H$ (CDCl$_3$) 2.42 (2H, br s, tetrahydropyridinyl CH$_2$), 2.68 (2H, br s, tetrahydropyridinyl CH$_2$), 3.14 (2H, br s, tetrahydropyridinyl CH$_2$), 3.68 (2H, s, ArCH$_2$N), 5.79 (1H, br s, tetrahydropyridinyl 5-CH), 6.42 (1H, d, J 16.2 Hz, ArCH=CHC), 6.69 (1H, d, J 16.2 Hz, ArCH=CHC), 6.99 (2H, d, J 8.7 Hz, 3'-H, 5'-H), 7.33–7.37 (2H, m, ArH), 7.51 (2H, d, J 7.9 Hz, ArH), and 7.62 (2H, d, J 8.2 Hz, ArH); m/z (ES$^+$) 319 (M+1)$^+$.

EXAMPLE 16

(E)-1-(3-Methoxybenzyl)-4-(2-phenylethenyl)-1,2,3,6-tetrahydropyridine

Step 1: (E)-4-(2-Phenylethenyl)pyridine

A mixture of phenyl iodide (100 ml, 0.89 mol), 4-vinylpyridine (115 ml, 1.07 mol), palladium acetate (2.4 g, 0.01 mol), tri-o-tolylphosphine (6.08 g, 0.02 mol) and triethylamine (150 ml, 1.07 mol) was refluxed for 3 hours. The reaction was cooled to room temperature, the resulting solid dissolved in dichloromethane (2 l) and washed with saturated aqueous sodium carbonate solution (2 l). The aqueous phase was further extracted with dichloromethane (3×1.5 l) and the combined organic phases dried (MgSO$_4$) and evaporated. The resulting solid was washed with ethyl acetate (1.5 l), filtered and dried in vacuo to give (E)-4-(2-phenylethenyl)pyridine (90 g, 56%); $\delta_H$ (CDCl$_3$) 7.01 (1H, d, J 16.3 Hz, ArCH=CH), 7.25–7.41 (6H, m, PhH, ArCH=CH), 7.53 (2H, d, J 5.3 Hz, 3-H, 5-H), and 8.58 (2H, d, J 5.2 Hz, 2-H, 6-H).

Step 2: (E)-1-(3-Methoxybenzyl)-4-(2-phenylethenyl)-1,2,3,6-tetrahydropyridine

To a solution of the foregoing pyridine (1 g, 5.5 mmol) in DMF (5 ml) was added 3-methoxybenzyl chloride (0.96 ml, 6.6 mmol) and the reaction heated at 90° C. for 1 hour. The reaction was cooled and the solvent evaporated. Ethanol (50 ml) was added to the residual solid, followed by portionwise addition of sodium borohydride (250 mg, 6.6 mmol). The reaction was stirred at room temperature for 2 hours, after which the solvent was evaporated to a slurry. Methanol (10 ml) was added and the mixture stood overnight. The resulting solid was removed by filtration, dried and recrystallised from methanol to yield the title compound (350 mg, 22%), m.p. 75°–77° C. (Found C, 79.33; H, 7.32; N, 4.46. C$_{21}$H$_{23}$NO. 0.6H$_2$O requires C, 79.76; H, 7.71; N, 4.43%); $\delta_H$ (CDCl$_3$) 2.41 (2H, br s, tetrahydropyridinyl CH$_2$), 2.67 (2H, t, J 5.8 Hz, tetrahydropyridinyl CH$_2$), 3.14 (2H, br s, tetrahydropyridinyl CH$_2$), 3.60 (2H, s, ArCH$_2$N), 3.81 (3H, s, OCH$_3$), 5.82 (1H, br s, tetrahydropyridinyl 5-CH), 6.44 (1H, d, J 16.2 Hz, ArCH=CHC), 6.77–6.82 (2H, m, ARCH=CHC, ArH), 6.94 (2H, m, ArH), 7.17–7.32 (4H, m, ArH), and 7.38–7.41 (2H, m, ArH); m/z (ES$^+$) 306 (M+1)$^+$.

EXAMPLE 17

(E)-t-Benzyl-4-[2-(indol-5-yl)ethenyl]-1,2,3,6-tetrahydropyridine hydrogen oxalate M.p. 120°–122° C. (dec.) (MeOH); (Found: C, 71.34; H, 5.85; N, 6.81. C$_{24}$H$_{24}$N$_2$O$_4$ requires C, 71.27; H, 5.98; N, 6.93%); $\delta_H$ (DMSO-d$_6$) 2.55 (2H, br s, tetrahydropyridinyl CH$_2$), 3.14 (2H, m, tetrahydropyridinyl CH$_2$), 3.52 (2H, br s, tetrahydropyridinyl CH$_2$), 4.13 (2H, s, PhCH$_2$N), 5.80 (1H, s, tetrahydropyridinyl CH), 6.40 (1H, br s, 3'-H), 6.64 (1H, d, J 16.2 Hz, CH=CHAr), 6.83 (2H, d, J 16.1 Hz, CH=CHAr), 7.27–7.36 (3H, m, ArH), 7.40–7.49 (5H, m, ArH), 7.62 (1H, s, ArH), and 11.12 (1H, br s, NH); m/z (ES$^+$) 315 (M+1)$^+$.

EXAMPLE 18

(E)-1-(4-Chlorobenzyl)-4-[2-(indol-5-yl)ethenyl]-1,2,3,6-tetrahydropyridine

M.p. 165°–166C. (EtOAc/60°–80° Petrol); (Found: C, 75.85; H, 5.97; N, 7.98. $C_{22}H_{21}ClN_2$ requires C, 75.74; H, 6.07; N, 8.03%); $\delta_H$ (CDCl$_3$) 2.46 (2H, br s, tetrahydropyridinyl CH$_2$), 2.69 (2H, t, J 7.5 Hz, tetrahydropyridinyl CH$_2$), 3.14 (2H, br s, tetrahydropyridinyl CH$_2$), 3.61 (2H, s, ArCH$_2$N), 5.76 (1H, br s, tetrahydropyridinyl CH), 6.52 (1H, m, 3'-H), 6.58 (1H, d, J 16.1 Hz, CH=CHAr), 6.77 (1H, d, J 16.1 Hz, CH=CHAr), 7.18 (1H, m, 2'-H), 7.28–7.34 (6H, m, ArH), 7.64 (1H, s, 4'-H), and 8.15 (1H, br s, NH); m/z (ES$^+$) 349 (M+1)$^+$.

EXAMPLE 19

(E)-1-Benzyl-4-[2-(2-chloropyridin-5-yl)ethenyl]-1,2,3,6-tetrahydropyridine

M.p. 126°–128° C. (MeOH); (Found: C, 73.75; H, 6.01; N, 9.12. $C_{19}H_{19}ClN_2$ requires C, 73.42; H, 6.16; N, 9.01%); $\delta_H$ (CDCl$_3$) 2.40 (2H, br s, tetrahydropyridinyl CH$_2$), 2.68 (2H, t, J 5.7 Hz, tetrahydropyridinyl CH$_2$), 3.14 (2H, m, tetrahydropyridinyl CH$_2$), 3.63 (2H, s, PhCH$_2$N), 5.89 (1H, s, tetrahydropyridinyl CH), 6.35 (1H, d, J 16.2 Hz, ArCH=CH), 6.80 (1H, d, J 16.2 Hz, ArCH=CH), 7.24–7.37 (6H, m, ArH), 7.67 (1H, dd, J 8.3, 2.4 Hz, 4'-H), and 8.34 (1H, d, J 2.3 Hz, 6'-H); m/z (ES$^+$) 311 (M+1)$^+$.

EXAMPLE 20

(E)-1-Benzyl-4-(2-(1-methylindol-5-yl)ethenyl)-1,2,3,6-tetrahydropyridine

Step 1: (E)-4-(1-Methylindol-5-yl)ethenylpyridine

Sodium hydride, 60% dispersion in oil (0.57 g, 14 mmol) was added portionwise to a suspension of (E)-4-(indol-5-yl)ethenylpyridine (2.82 g, 12.8 mmol) [prepared from 4-vinylpyridine and 5-bromoindole by an analogous procedure to Example 16] in dimethylformamide (100 ml). The mixture was stirred at room temperature, under nitrogen, for 1.5 h to give a red solution which was then cooled to 0° C. and treated dropwise with methyl iodide (0.88 ml, 14 mmol). The reaction mixture was stirred at 0° C. under nitrogen for 10 min, allowed to warm to room temperature and stirred for a further 30 min. The resulting suspension was diluted with water (200 ml), the solid collected under suction, washed with 5% aqueous sodium sulfite solution then water and dried in vacuo to afford the title compound as a buff solid (3.07 g); $\delta_H$ (CDCl$_3$) 3.81 (3H, s, N-CH$_3$), 6.51 (1H, dd, J 3.1, 0.7 Hz, 3'-H), 6.98 (1H, d, J 16.3 Hz, CH=CH), 7.07 (1H, d, J 3.1 Hz, 2'-H), 7.31–7.51 (5H, m, CH=CH, ArH), 7.78 (1H, d, J 1.4 Hz, 4'-H), 8.55 (2H, m, 2-H, 6-H-1).

Step 2: (E)-Benzyl-4-(2-(1-methylindol-5-yl)ethenyl)-1,2,3,6-tetrahydropyridine

The title compound was prepared from (E)-4-(1-methylindol-5-yl)ethenylpyridine by an analogous procedure to Example 1, m.p. 137.5°–138.5° C. (MeOH); (Found: C, 84.17; H, 7.11; N, 8.48. $C_{23}H_{24}N_2$ requires C, 84.11; H, 7.37; N, 8.53%); $\delta_H$ (CDCl$_3$) 2.45 (2H, br s, tetrahydropyridinyl CH$_2$), 2.68 (2H, m, tetrahydropyridinyl CH$_2$), 3.13 (2H, br s, tetrahydropyridinyl CH$_2$), 3.63 (2H, s, PhCH$_2$N), 3.77 (3H, s, N-CH$_3$), 5.77 (1H, br s, tetrahydropyridinyl CH), 6.43 (1H, m, 3'-H), 6.58 (1H, d, J 16.1 Hz, CH=CHAr), 6.77 (1H, d, J 16.1 Hz, CH=CHAr), 7.00 (1H, d, J 3.1 Hz, 2'-H), 7.23–7.39 (7H, m, ArH), and 7.61 (1H, s, ArH); m/z (ES$^+$) 329 (+1)$^+$.

EXAMPLE 21

(E)-1-Benzyl-4-(2-(3-fluoro-4-methoxy)phenylethenyl)-1,2,3,6-tetrahydropyridine

M.p. 124°–124.5° C. (EtOAc/60°–80° Petrol); (Found: C, 77.44; H, 6.57; N, 4.59. $C_{21}H_{22}FNO.0.1H_2O$ requires C, 77.56; H, 6.88; N, 4.31%); $\delta_H$ (CDCl$_3$) 2.39 (2H, br s, tetrahydropyridinyl CH$_2$), 2.67 (2H, t, J 5.7 Hz, tetrahydropyridinyl CH$_2$), 3.13 (2H, m, tetrahydropyridinyl CH$_2$), 3.16 (2H, s, PhCH$_2$N), 3.88 (3H, s, ArOCH$_3$), 5.79 (1H, m, tetrahydropyridinyl CH), 6.33 (1H, d, J 16.1 Hz, CH=CHAr), 6.64 (1H, d, J 16.1 Hz, CH=CHAr), 6.88 (1H, t, J 8.6 Hz, 5'-H), 7.06 (1H, m, 6'-H), 7.16 (1H, dd, J 12.7, 2.1 Hz, 2'-H), and 7.24–7.38 (5H, m, PhH); m/z (ES$^+$) 324 (M+1)$^+$.

EXAMPLE 22

(E)-1-(4-Methoxybenzyl)-4-(2-phenylethenyl)-1,2,3,6-tetrahydropyridine

M.p. 144°–146° C. (MeOH); (Found: C, 82.67; H, 7.68; N, 4.55. $C_{21}H_{23}NO$ requires C, 82.58; H, 7.59; N, 4.59%); $\delta_H$ (CDCl$_3$) 2.41 (2H, br s, tetrahydropyridinyl CH$_2$), 2.65 (2H, t, J 5.8 Hz, tetrahydropyridinyl CH$_2$), 3.12 (2H, br s, tetrahydropyridinyl CH$_2$), 3.56 (2H, s, ArCH$_2$N), 3.81 (3H, s, OCH$_3$), 5.81 (1H, br s, tetrahydropyridinyl 5-CH), 6.43 (1H, d, J 16.2 Hz, ArCH=CHC), 6.78 (1H, d, J 16.2 Hz, ArCH=CHC), 6.86 (2H, d, J 7.2 Hz, 3'- H, 5'-H), 7.19 (1H, t, J 7.3 Hz, ArH), 7.25–7.31 (4H, m, ArH), and 7.39 (2H, d, J 7.2 Hz, 2'-H, 6'-H); m/z (ES$^+$) 306 (M+1)$^+$.

EXAMPLE 23

(E)-1-(4-Chlorobenzyl)-4-(2-phenylethenyl)-1,2,3,6-tetrahydropyridine

M.p. 141°–142° C. (MeOH); (Found: C, 77.41; H, 6.35; N, 4.53. $C_{20}H_{20}ClN$ requires C, 77.53; H, 6.51; N, 4.52%); $\delta_H$ (CDCl$_3$) 2.42 (2H, br s, tetrahydropyridinyl CH$_2$), 2.65 (2H, t, J 5.8 Hz, tetrahydropyridinyl CH$_2$), 3.11 (2H, br s, tetrahydropyridinyl CH$_2$), 3.58 (2H, s, ArCH$_2$N), 5.81 (1H, br s, tetrahydropyridinyl 5-CH), 6.44 (1H, d, J 16.2 Hz, ArCH=CHC), 6.78 (1H, d, J 16.2 Hz, ArCH=CHC), and 7.18–7.41 (9H, m, ArH); m/z (ES$^+$) 310 (M+1)$^+$.

EXAMPLE 24

(E)-1-(4-Fluorobenzyl)-4-(2-phenylethenyl)-1,2,3,6-tetrahydropyridine

M.p. 115°–117° C. (MeOH); (Found: C, 81.50; H, 6.51; N, 4.84. $C_{20}H_{20}FN$ requires C, 81.88; H, 6.87; N, 4.77%); $\delta_H$(CDCl$_3$) 2.41 (2H, br s, tetrahydropyridinyl CH$_2$), 2.66 (2H, t, J 5.8 Hz, tetrahydropyridinyl CH$_2$), 3.11 (2H, br s, tetrahydropyridinyl CH$_2$), 3.58 (2H, s, ArCH$_2$N), 5.81 (1H, br s, tetrahydropyridinyl 5-CH), 6.44 (1H, d, J 16.1 Hz, ArCH=CHC), 6.78 (1H, d, J 16.1 Hz, ArCH=CHC), 7.01 (2H, t, J 8.7 Hz, ArH), and 7.17–7.40 (7H, m, ArH); m/z (ES$^+$) 294 (M+1)$^+$.

EXAMPLE 25

(E)-1-(4-Chlorobenzyl)-4-[2-(4-chlorophenyl)ethenyl]-1,2,3,6-tetrahydropyridine

M.p. 127°–129C. (MeOH); (Found: C, 69.87; H, 5.21; N, 4.07. $C_{20}H_{19}Cl_2N$ requires C, 69.77; H, 5.56; N, 4.07%); 5H (CDCl$_3$) 2.39 (2H, br s, tetrahydropyridinyl CH$_2$), 2.65 (2H, t, J 5.8 Hz, tetrahydropyridinyl CH$_2$), 3.19 (2H, br s, tetrahydropyridinyl CH$_2$), 3.58 (21h, s, ArCH$_2$N), 5.82 (1H, br s, tetrahydropyridinyl 5-CH), 6.38 (1 7, d, J 16.1 Hz, ArCH=CHC), 6.75 (1H, d, J 16.1 Hz, ArCH=CHC), and 7.25–7.33 (81, m, ArH); m/z (ES$^+$) 344 (M+1)$^+$.

EXAMPLE 26

(E)-1-Benzyl-4-[2-(3-methanesuphonylphenyl)ethenyl]-1,2,3,6-tetrahydropyridine

Step 1: 1-Bromo-3-methanesulphonylbenzene

To a solution of 3-bromothioanisole (6.6 g, 32.5 mmol) in dichloromethane (100 ml) was added a solution of meta-chloroperbenzoic acid (55%, 11.4 g, 66 mmol) in dichloromethane (150 ml) via dropping funnel. After stirring at room temperature for 2 hours, the reaction mixture was washed with saturated aqueous sodium carbonate solution (250 ml). The aqueous phase was extracted with dichloromethane (2×250 ml), the combined organics dried (MgSO$_4$) and evaporated to give 1-bromo-3-methanesulphonylbenzene as a solid (7.7 g, 100%); $\delta_H$ (CDCl$_3$) 3.07 (31, s, SO$_2$CH$_3$), 7.45 (1, t, J 8.1 Hz, 5-H), 7.79 (1H, d, J 8.1 H z, 6-H), 7.90 (1H, d, J 8.1 Hz, 4-H), and 8.10 (1H, s, 2-H).

Step 2: (E)-1-Benzyl-4-[2-(3-methanesulphonylphenyl)ethenyl]-1,2,3,6-tetrahydropyridine The product from Step 1 was elaborated by the method outlined in Example 16 to give the title compound:

M.p. 150°–152° C. (MeOH); (Found: C, 71.28; H, 6.28; N, 4.03. C$_{21}$H$_{23}$NO$_2$S requires C, 71.36; H, 6.56; N, 3.99%); $\delta_H$ (DMSO-d$_6$) 2.35 (2H, br s, tetrahydropyridinyl CH$_2$), 3.07 (2H, br s, tetrahydropyridinyl CH$_2$), 3.24 (3H, SO$_2$CH$_3$), 3.59 (2H, 3 , ArCH$_2$N), 6.00 (1H, s, tetrahydropyridinyl 5-CH), 6.61 (1H, d, J 16.2 Hz, ArCH=CHC), 7.08 (1H, d, J 16.2 Hz, ArCH=CHC), 7.28 (FH, t, J 4.3 Hz, 4-H), 7.34–7.35 (4H, m, ArH), 7.60 (1H, t, J 7.8 Hz, 5'-H), 7.75 (1H, d, J 7.8 Hz, 6'-H), 7.83 (1H, d, J 7.8 Hz, 4'-H), and 8.01 (1H, s, 2'-H); m/z (ES$^+$) 354 (M+1)$^+$.

EXAMPLE 27

(E)-1-(3,4-Dichlorobenzyl)-4-(2-phenylethenyl)-1,2,3,6-tetrahydropyridine

Step 1: (E)-4-(2-Phenylethenyl)-,1,2,3,6-tetrahydropyridine hydrochloride

To a solution of (E)-1-benzyl-4-(2-phenylethenyl)-1,2,3,6-tetrahydropyridine (27 g, 100 mmol) in dichloromethane (400 ml) at 0° C. was added 1-chloroethyl chloroformate (13 ml, 120 mmol) via syringe, keeping the temperature below 5° C. The reaction was stirred at 0° C. for 1 hour and then warmed to room temperature over 2 hours. The solvent was evaporated, methanol (500 ml) added to the residue, and the reaction refluxed for 90 minutes. The reaction was cooled to room temperature, the solvent evaporated to a slurry and ether (≈200 ml) added. The resultant solid was filtered and dried to give the title compound (17 g, 77%); $\delta_H$ (DMSO-d$_6$) 2.55 (2H, br s, tetrahydropyridinyl CH$_2$), 3.25 (2H, br s, tetrahydropyridinyl CH$_2$), 3.71 (2H, br s, tetrahydropyridinyl CH$_2$), 5.92 (1H, br s, tetrahydropyridinyl 5-CH), 6.62 (1H, d, J 16.3 Hz, ArCH=CHC), 6.97 (1H, d, J 16.3 Hz, ArCH=CHC), 7.25 (1H, d, J 7.3 Hz, 4-H), 7.35 (2H, t, J 7.3 Hz, 3-H, 5-H), 7.52 (2H, d, J 7.3 Hz, 2-H, 6-H), and 9.51 (1H, br s, NH); m/z (ES$^+$) 306 (M+1)$^+$.

Step 2: (E)-1-(3,4-Dichlorobenzyl-4-(2-phenylethenyl)-1,2,3,6-tetrahydropyridine A mixture of the foregoing tetrahydropyridine hydrochloride (750 mg, 3.4 mmol), 3,4-dichlorobenzyl bromide (888 mg, 3.7 mmol) and potassium carbonate (966 mg, 7 mmol) in DMF (10 ml) was stirred at room temperature for 48 hours. The reaction was diluted with water (50 ml) and extracted with ethyl acetate (4×50 ml). The combined organic phases were dried (MgSO$_4$) and evaporated to a solid, which was recrystallised from methanol to give the title compound (500 mg, 43%), m.p. 123°–125° C.; (Found: C, 69.68; H, 5.63; N, 4.22. C$_{20}$H$_{19}$Cl$_2$N requires C, 69.77; H, 5.56; N, 4.07%); $\delta_H$ (CDCl$_3$) 2.42 (2H, br s, tetrahydropyridinyl CH$_2$), 2.68 (2H, t, J 5.8 Hz, tetrahydropyridinyl CH$_2$), 3.12 (2H, br s, tetrahydropyridinyl CH$_2$), 3.56 (2H, s, ArCH$_2$N), 5.81 (1H, br s, tetrahydropyridinyl 5-CH), 6.46 (1H, d, J 16.2 Hz, ArCH=CHC), 6.79 (2H, d, J 16.2 Hz, ArCH=CHC), 7.18–7.32 (4H, m, ArH), 7.37–7.41 (3H, m, ArH), and 7.48 (1H, s, 2-H); m/z (ES$^+$) 344 (M+1)$^+$.

EXAMPLE 28

(E)-1-(4-Methylbenzyl)-4-(2-phenylethenyl)-1,2,3,6-tetrahydropyridine

M.p. 117°–119° C. (MeOH); (Found: C, 86.91; H, 8.05; N, 4.72. C$_{21}$H$_{23}$N requires C, 87.15; H, 8.01; N, 4.84%); $\delta_H$ (CDCl$_3$) 2.35 (3H, s, ArCH$_3$), 2.42 (2H, br s, tetrahydropyridinyl CH$_2$), 2.67 (2H, t, J 5.7 Hz, tetrahydropyridinyl CH$_2$), 3.13 (2H, br s, tetrahydropyridinyl CH$_2$), 3.59 (2H, s, ArCH$_2$N), 5.81 (1H, br s, tetrahydropyridinyl 5-CH), 6.44 (1H, d, J 16.2 Hz, ArCH=CHC), 6.78 (1H, d, J 16.2 Hz, ArCH=CHC), 7.12–7.31 (7H, m, ArH), and 7.39 (2H, d, J 7.3 Hz, ArH); m/z (ES$^+$) 290 (M+1)$^+$.

EXAMPLE 29

(E)-1-(4-Cyanobenzyl)-4-(2-phenylethenyl)-1,2,3,6-tetrahydropyridine

M.p. 155°–157° C. (MeOH); (Found: C, 83.66; H, 6.65; N, 9.17. C$_{21}$H$_{20}$N$_2$ requires C, 83.96; H, 6.71; N, 9.33%); $\delta_H$ (CDCl$_3$) 2.44 (2H, br s, tetrahydropyridinyl CH$_2$), 2.69 (2H, t, J 5.7 Hz, tetrahydropyridinyl CH$_2$), 3.15 (2H, br s, tetrahydropyridinyl CH$_2$), 3.68 (2H, s, ArCH$_2$N), 5.81 (1H, br s, tetrahydropyridinyl 5-CH), 6.46 (1H, d, J 16.2 Hz, ArCH=CHC), 6.79 (1H, d, J 16.2 Hz, ArCH=CHC), 7.19–7.32 (3H, m, ArH), 7.40 (2H, d, J 7.4 Hz, ArH), 7.51 (2H, d, J 8.2 Hz, ArH), and 7.62 (2H, d, J 8.2 Hz, ArH); m/z (ES$^+$) 301 (M+1)$^+$.

EXAMPLE 30

(E)-1-(4-Chlorobenzyl)-4-[2-(3-chlorophenyl)ethenyl]-1,2,3,6-tetrahydropyridine

M.p. 94°–96° C. (MeOH); (Found: C, 69.85; H, 5.58; N, 4.21. C$_{20}$H$_{19}$Cl$_2$N requires C, 69.77; H, 5.56; N, 4.07%); $\delta_H$ (CDCl$_3$) 2.39 (2H, br s. tetrahydropyridinyl CH$_2$), 2.66 (2H, t, J 5.8 Hz, tetrahydropyridinyl CH$_2$), 3.13 (2H, br s, tetrahydropyridinyl CH$_2$), 3.59 (2H, s, ArCH$_2$N), 5.84 (1H, br s, tetrahydropyridinyl 5-CH), 6.37 (1H, d, J 16.1 Hz, ArCH=CHC), 6.77 (1H, d, J 16.1 Hz, ArCH=CHC), and 7.14–7.38 (8H, m, ArH); m/z (ES$^+$) 344 (M+1)$^+$.

EXAMPLE 31

(E)-1-(4-Nitrobenzyl)-4-(2-phenylethenyl)-1,2,3,6-tetrahydropyridine

M.p. 142°–144° C. (MeOH); (Found: C, 74.45; H, 5.94; N, 8.76. C$_{20}$H$_{20}$N$_2$O$_2$ requires C, 74.77; H, 6.30; N, 8.72%); $\delta_H$ (CDCl$_3$) 2.45 (2H, br s, tetrahydropyridinyl CH$_2$), 2.70 (2H, t, J 5.4 Hz, tetrahydropyridinyl CH$_2$), 3.16 (2H, br s, tetrahydropyridinyl CH$_2$), 3.72 (2H, s, ArCH$_2$N), 5.81 (1H, br s, tetrahydropyridinyl 5-CH), 6.47 (1H, d, J 16.1 Hz, ArCH=CHC), 6.79 (1H, d, J 16.2 Hz, ArCH=CHC), 7.19–7.33 (3H, m, ArH), 7.40 (2H, d, J 7.2 Hz, ArH), 7.57 (2H, d, J 8.4 Hz, 2'-H, 6'-H), and 8.19 (2H, d, J 8.4 Hz, 3'-H, 5'-H); m/z (ES$^+$) 321 (M+1)$^+$.

EXAMPLE 32

(E)-4-[2-(3-Chlorophenyl)ethenyl]1-(4-methylbenzyl)-1,2,3,6-tetrahydropyridine

M.p. 86°–88° C. (MeOH); (Found: C, 77.74; H, 6.72; N, 4.35. C$_{21}$H$_{20}$ClN requires C, 77.88; H, 6.85; N, 4.32%); $\delta_H$ (CDCl$_3$) 2.35 (3H, s, ArCH$_3$), 2.40 (2H, br s, tetrahydropyridinyl CH$_2$), 2.67 (2H, t, J 5.7 Hz, tetrahydropyridinyl CH$_2$), 3.14 (2H, br s, tetrahydropyridinyl CH$_2$), 3.60 (2H, s, ArCH$_2$N), 5.84 (1H, br s, tetrahydropyridinyl 5-CH), 6.36 (1H, d, J 16.1 Hz, ArCH=CHC), 6.77 (1H, d, J 16.1 Hz, ArCH=CHC), 7.08–7.26 (7H, m, ArH), and 7.38 (1H, s, 2-H); m/z (ES$^+$) 324 (M+l)$^+$.

EXAMPLE 33

(E)-1-(4-Iodobenzyl)-4-(2-phenylethenyl)-1,2,3,6-tetrahydropyridine

Step 1: 4-Iodobenzyl bromide

A mixture of 4-iodotoluene (21.8 g, 100 mmol), N-bromosuccinimide (18.69 g, 105 mmol) and αα-azobisisobutyronitrile (100 mg) in carbon tetrachloride (100 ml) was refluxed for 20 hours. The reaction was cooled, the precipitate filtered, washed with carbon tetrachloride (50 ml), and the filtrate evaporated. The residue was chromatographed on silica, eluting with petrol (60°–80° C.) to give the product as a white solid (13 g, 45%); $\delta_H$ (CDCl$_3$) 4.42 (2H, ArCH$_2$Br), 7.11 (2H, d, J 15.3 Hz, 2-H, 6-H), 7.67 (2H, d, J 15.3 Hz, 3'-H, 5'-H).

Step 2: (E)-1-(4-Iodobenzyl)-4-(2-phenylethenyl)-1,23,6-tetrahydropyridine

The product from Step 1 was taken on as before to give the title compound.

M.p. 133°–135° C. (methanol); (Found: C, 59.78, H, 4.93; N, 3.51. C$_{20}$H$_{20}$IN requires C, 59.86; H, 5.02; N, 3.49%); $\delta_H$ (CDCl$_3$) 2.44 (2H, br s, tetrahydropyridinyl CH$_2$), 2.69 (2H, br s, tetrahydropyridinyl CH$_2$), 3.15 (2H, br s, tetrahydropyridinyl CH$_2$), 3.59 (2H, s, ArCH$_2$N), 5.80 (1H, br s, tetrahydropyridinyl 5-CH), 6.45 (1H, d, J 16.1 Hz, ArCH=CHC), 6.78 (1H, d, J 16.1 Hz, ArCH=CHC), 7.16–7.32 (5H, m, ArH), 7.39 (5H, m, ArH), 7.39 (2H, d, J 7.3 Hz, 2-H, 6-H), and 7.66 (2H, d, J 7.3 Hz, 3'-H, 5-H); m/z (ES$^+$) 402 (M+1)$^+$.

EXAMPLE 34

(E)-4-(2-Phenylethenyl)-1-(4-trifluoromethylbenzyl)-1,2,3,6-tetrahydropyridine

M.p. 125°–127° C. (MeOH); (Found: C, 73.83; H, 5.82; N, 4.13. C$_{21}$H$_{20}$F$_2$N requires C. 73.45; H, 5.87; N, 4.08%); $\delta_H$ (CDCl$_3$) 2.45 (2H, br s, tetrahydropyridinyl CH$_2$), 2.71 (2H, br s, tetrahydropyridinyl CH$_2$), 3.17 (2H, br s, tetrahydropyridinyl CH$_2$), 3.70 (2H, s, ArCH$_2$N), 5.81 (1H, br s, tetrahydropyridinyl 5-CH), 6.46 (1H, d, J 16.1 Hz, ArCH=CHC), 6.79 (1H, d, J 16.1 Hz, ArCH=CHC), 7.18–7.32 (3H, m, ArH), 7.40 (2H, d, 7.3 Hz, ArH), 7.52 (2H, d, J 7.7 Hz, 2'-H, 6'-H), and 7.59 (2H, d, J 7.7 Hz, ArH); m/z (ES$^+$) 344 (M+1)$^+$.

EXAMPLE 35

(E)-4-[2-(4-Chlorophenyl)ethenyl]-1-(4-methylbenzyl)-1,2,3,6-tetrahydropyridine

M.p. 113–115° C. (MeOH); (Found: C, 77.54; H, 6.65; N, 4.43. C$_{21}$H$_{20}$ClN requires C, 77.88; H, 6.84; N, 4.32%); $\delta_H$ (CDCl$_3$) 2.35 (3H, s, ArCH$_3$), 2.42 (2H, br s, tetrahydropyridinyl CH$_2$), 2.67 (2H, br s, tetrahydropyridinyl CH$_2$), 3.14 (2H, br s, tetrahydropyridinyl CH$_2$), 3.60 (2H, s, ArCH$_2$N), 5.82 (1H, br s, tetrahydropyridinyl 5-CH), 6.38 (1H, d, J 16.1 Hz, ArCH=CHC), 6.74 (1H, d, J 16.1 Hz, ArCH=CHC), 7.14 (2H, d, J 7.9 Hz, ArH), and 7.24∝7.32 (6H, m, ArH); m/z (ES$^+$) 324 (M+1)$^+$.

EXAMPLE 36

(E)-1-(Indol-5-yl)methyl-4-(2-phenylethenyl)-1,2,3,6-tetrahydropyridine

Step 1: (Indol-5-yl)-(4-(2-phenylethenyl)-1,2,3,6-tetrahydropyridin-1- yl)methanone 1-(3-Dimethylaminopropyl)-3-ethylcarbodiimide hydrochloride (0.77 g, 4.02 mmol) was added to a mixture of indole-5-carboxylic acid (0.45 g, 2.79 mmol), (E)-4-(2-phenylethenyl)-1,2,3,6-tetrahydropyridine hydrochloride (0.59 g, 2.66 mmol), 1-hydroxybenzotriazole hydrate (0.56 g, 3.3 mmol) and triethylamine (1.1 ml, 7.9 mmol) in dimethylformamide (20 ml). The reaction mixture was stirred at room temperature, under nitrogen, overnight then poured into water (200 ml) and extracted with ethyl acetate (2×100 ml). The extracts were washed with 1M hydrochloric acid (2×100 ml), saturated brine (100 ml), combined and dried (MgSO$_4$). The residue after evaporation of the solvent was purified by flash chromatography, eluting with 2:1, 3:1 then 4:1 ethyl acetate/petrol (60°–80°), to afford the title compound as an off-white solid (0.55 g, 63%); $\delta_H$ (CDCl$_3$) 2.50 (2H, br s, tetrahydropyridinyl CH$_2$), 3.76 (2H, v br s, tetrahydropyridinyl CH$_2$), 4.31 (2H, v br s, tetrahydropyridinyl CH$_2$), 5.84 (1H, v br s, tetrahydropyridinyl CH), 6.51 (1H, d, J 16.2 Hz, CH=CHPh), 6.60 (1H, br s, 3'-H), 6.81 (1H, d, J 16.2 Hz, CH=CHPh), 7.20–7.42 (9H, m, ArH), 7.42 (1H, s, ArH), and 8.46 (1H, br s, NH).

Step 2: (E)-1-(Indol-5-yl)methyl-4-(2-phenylethenyl)-1,2,3,6-tetrahydropyridine

A solution of lithium aluminium hydride in tetrahydrofuran (1.0M; 1.0 ml, 1.0 mmol) was added to a suspension of the foregoing amide (0.27 g, 0.82 mmol) in tetrahydrofuran (15 ml) and the mixture heated at reflux under nitrogen for 30 minutes. The reaction mixture was allowed to cool and then treated successively with water (0.05 ml), 4M sodium hydroxide (0.05 ml) and water (0.15 ml). The mixture was stirred for a few minutes, filtered and the filter cake washed with tetrahydrofuran then dichloromethane. The filtrate was concentrated in vacuo and the residue recrystallised from methanol to afford the title compound as a cream solid (0.0756 g, 29%), m.p. 214°–216° C. (dec.); (Found: C, 83.77; H, 7.10; N, 8.77. C$_{21}$H$_{22}$N$_2$ requires C, 84.04; H, 7.05; N, 8.19%); $\delta_H$ (CDCl$_3$) 2.41 (2H, br s, tetrahydropyridinyl CH$_2$), 2.71 (2H, t, J 5.8 Hz, tetrahydropyridinyl CH$_2$), 3.16 (2H, br s, tetrahydropyridinyl CH$_2$), 3.72 (2H, s, ArCH$_2$N), 5.82 (1H, br s, tetrahydropyridinyl CH), 6.43 (1H, d, J 16.2 Hz, CH=CHPh), 6.52 (1H, m, 3'-H), 6.79 (1H, d, J 16.2 Hz, CH=CHPh), 7.16–7.40 (8H, m, ArH), 7.60 (1H, s, ArH), and 8.17 (1H, br s, NH); m/z (ES$^+$) 315 (M+1)$^+$.

EXAMPLE 37

(E)-5-(4-[2-Phenylethenyl]-1,2,3,6-tetrahydropyridin-1-yl) methyl benzimidazole dihydrochloride Step 1: (E)-Benzimidazol-5-yl-(4-[2-phenylethenyl]-1,2,3,6-tetrahydropyridin-1-yl)methanone A suspension of benzimidazole-5-carboxylic acid (1.62 g, 10 mmol) in thionyl chloride (20 ml) was stirred under reflux for 5 h, and, after cooling, filtered to leave the acid chloride hydrochloride as a white solid (1.91 g). A portion of this solid (1.09 g, 5 mmol) was stirred with (E)-4-(2-phenylethenyl)-1,2,3,6-tetrahydropyridine hydrochloride (1.11 g, 5 mmol) in acetonitrile (30 ml) in the presence of triethylamine (2.8 ml, 20 mmol) for 2.5 days. The resulting suspension was filtered, the filtrate evaporated and the residue combined with the solid collected and partitioned between aqeuous sodium hydroxide (4M, 50 ml) and ethyl acetate (2×25 ml). The organic layers were dried (MgSO$_4$), evaporated, and the residue subjected to chromatography on silica gel, eluting with 10% methanol in dichloromethane, to leave the product as a pale brown foam (0.90 g).

Step 2: (E)-5-(4-[2-Phenylethenyl]1,2,3,6-tetrahydropyridin-1-yl)methyl benzimidazole dihydrochloride To a suspension of the foregoing amide (0.88 g, 2.7 mmol) in DME (40 ml) was added lithium aluminium hydride in THF (1M, 10 ml) and the mixture stirred at room temperature for 2.5 days, before adding ethyl acetate (5 ml). This was followed after 15 min by sequential addition of water (0.38 ml), aqueous sodium hydroxide (4M, 0.38 ml), and water (1.2 ml), and the mixture stirred for 0.5 h before being filtered and the filtrate evaporated. The residue was chromatographed on silica gel (10% methanol in dichloromethane) to give a pale yellow foam (0.39 g). Treatment with ethereal HCl and recrystallisation from methanol/diethyl ether gave the title compound as an ochre solid (311 mg), m.p. 287°–290 C.; (Found: C, 63.61; H, 5.99; N, 10.39. $C_{21}H_{23}Cl_2N_3$ 0.5 $H_2O$ requires C, 63.48; H, 6.09; N, 10.58%); pH ($D_2$l) 2.76 (2H, in tetrahydropyridinyl $CH_2$), 3.36 (1H, br s, tetrahydropyridinyl $CH_2$), 3.77 (1H, br s, tetrahydropyridinyl $CH_2$), 3.89 (2H, br s, tetrahydropyridinyl $CH_2$), 4.63 (2H, s, Ar$CH_2$N), 5.86 (1H, s, —CH=C—), 6.68 (1H, d, J 16.4 Hz, —CH=CH—), 6.95 (1H, d, J 16.4 Hz, —CH=CH—), 7.33 (1H, t, J 7.3 Hz, 4'-H), 7.41 (2H, t, J 7.3 Hz, 3', 5'-H), 7.53 (2H, d, J 7.3 Hz, 2', 6'-H), 7.72 (1H, dd, J 8.6, 1.3 Hz, 6-H), 7.97 (1H, d, J 8.6 Hz, 7-H), 8.03 (1H, s, 4-H), and 9.18 (1H, s, 2-H); m/z (CI$^+$, NH$_3$) 316 (M+1)$^+$.

EXAMPLE 38
(E)-4-(4-[2-Phenylethenyl]-1,2,3,6-tetrahydropyridin-1-yl)methyl imidazole dihydrochloride Step 1: 1-(4-Methylphenylsulfonyl)-4-methanesulfonyloxymethyl imidazole Triethylamine (25.9 ml) was added dropwise to a suspension of 4-hydroxymethylimidazole hydrochloride (10.0 g, 74 mmol) in dichloromethane (200 ml) containing 4-methylbenzenesulfonyl chloride (15.6 g) and the mixture stirred overnight before being washed with water and brine, dried (MgSO$_4$), and evaporated to leave a colourless oil. This was chromatographed on silica gel, eluting with ethyl acetate/hexanes to give an oil which solidified on standing (15.0 g). A portion of this solid (1.0 g, 4 mmol) was dissolved in dichloromethane (15 ml), and the solution cooled in an ice bath as triethylamine (0.5 g), followed by methanesulfonyl chloride (0.55 g) in dichloromethane (1 ml) were added dropwise. After tlc indicated reaction to have completed, the mixture was washed with water and brine, then dried (MgSO$_4$), before evaporating to leave the product as a white powder (1.3 g).

Step 2: (E)-1-(4-Methylphenylsulfonyl)-4-(4-[2-phenylethenyl]-1,2,3,6-tetrahydropyridin-1-yl)methyl imidazole The foregoing mesylate (330 mg, 1.0 mmol) was stirred in DMF (10 ml) with (E)-4-(2-phenylethenyl)-1,2,3,6-tetrahydropyridine hydrochloride (222 mg, 1.0 mmol) and potassium carbonate (0.5 g, 3.6 mmol) for 2.5 days. The reaction mixture was poured into water (75 ml) and extracted with ethyl acetate (2×25 ml), the combined organic layers washed with brine (25 ml), dried (MgSO$_4$), and evaporated to leave the product as a yellow oil which solidified on standing (426 mg).

Step 3: (E)-4-(4-[2-Phenylethenyl]-1,2,3,6-tetrahydropyridin-1-yl)methyl imidazole dihydrochloride Ethereal HCl was added to a solution of the foregoing intermediate in dichloromethane (10 ml), and the resulting suspension stirred until the gum formed had settled and solidified. The supernatant was decanted, the residual solid triturated with a little ethyl acetate and then recrystallised from methanol to leave the title compound as a pale yellow solid (150 mg), m.p. 288°–291° C.; (Found: C, 60.21; H, 6.24; N, 12.28. $C_{17}H_{21}Cl_2N_3$ requires C, 60.36; H, 6.26; N, 12.42%); $\delta_H$ (D$_2$O) 2.78 (2H, br s, tetrahydropyridinyl CH$_2$), 3.59 (2H, br s, tetrahydropyridinyl CH$_2$), 3.94 (2H, br s, tetrahydropyridinyl CH$_2$), 4.65 (2H, s, ArCH$_2$N), 5.88 (1H, s, —CH=C—), 6.70 (1H, d, J 16.4 Hz, —CH=CH—), 6.96 (1H, d, J 16.4 Hz, —CH=CH—), 7.34 (1H, t, J 7.2 Hz, 4'-H), 7.42 (2H, t, J 7.3 Hz, 3', 5'-H), 7.54 (2H, d, J 7.3 Hz, 2', 6'-H), 7.82 (1H, s, 5-H), and 8.81 (1H, s, 2-H); m/z (CI$^+$, NH$_3$) 266 (M+1)$^+$.

We claim:

1. A pharmaceutical composition comprising a compound of formula 1, or a pharmaceutially acceptable salt thereof:

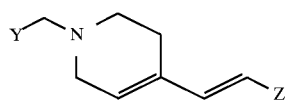

wherein
Y represents a group of formula (a), (b), or (c) and Z represents a group of formula (a), (b), (c) or (d):

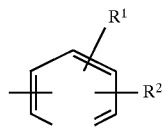

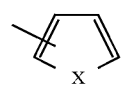

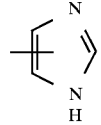

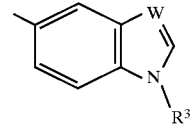

in which
W represents CH or nitrogen;
X represents oxygen, sulphur or N-R$^3$,
R$^1$ and R$^2$ independently represent hydrogen, halogen, cyano, nitro, trifluoromethyl, $C_{1-6}$ alkyl, $C_{1-6}$ alkoxy or $C_{1-6}$ alkylsulphonyl; or R$^1$ and R$^2$, when situated on adjacent carbon atoms, together represent methylenedioxy; and
R$^3$ represents hydrogen or $C_{1-6}$ alkyl; in association with a pharmaceutically acceptable carrier.

2. A method for the prevention and/or treatment of clinical conditions for which a dopamine receptor subtype ligand is indicated, which method comprises administering to a patient in need of such treatment an effective amount of a compound of formula I as defined in claim 1 or a pharmaceutically acceptable salt thereof.

3. A composition as claimed in claim 1 wherein the compound of formula I is (E)-1-benzyl-4-(2-phenylethenyl)-1,2,3,6-tetrahydropyridine.

4. A compound selected from:
(E)-1-benzyl-4-[2-(3,4-difluorophenyl)ethenyl]-1,2,3,6-tetrahydropyridine;
(E)-1-benzyl-4-[2-(3,5-difluorophenyl)ethenyl]-1,2,3,6-tetrahydropyridine;
(E)-1-benzyl-4-[2-(2-fluorophenyl)ethenyl]-1,2,3,6-tetrahydropyridine;
(E)-1-benzyl-4-[2-(thien-3-yl)ethenyl]-1,2,3,6-tetrahydropyridine;
(E)-1-benzyl-4-[2-(thien-2-yl)ethenyl]-1,2,3,6-tetrahydropyridine;
(E)-4-[2-(4'-cyanophenyl)ethenyl]-1-(4-methoxybenzyl)-1,2,3,6-tetrahydropyridine;
(E)-1-(4-chlorobenzyl)-4-[2-(4'-methylphenyl)ethenyl]-1,2,3,6-tetrahydropyridine;
(E)-1-(4-chlorobenzyl)-4-[2-(3,4-methylenedioxyphenyl)ethenyl]-1,2,3,6-tetrahydropyridine;
(E)-1-(4-methylbenzyl)-4-[2-(3,4-methylenedioxyphenyl)ethenyl]-1,2,3,6-tetrahydropyridine;

(E)-1-(4-chlorobenzyl)-4-[2-(thien-3-yl)ethenyl]-1,2,3,6-tetrahydropyridine;
(E)-4-[2-(4-fluorophenyl)ethenyl]-1-(4-methylbenzyl)-1,2,3,6-tetrahydropyridine;
(E)-1-(4-cyanobenzyl)-4-[2-(4-fluorophenyl)ethenyl]-1,2,3,6-tetrahydropyridine;
(E)-1-(3-methoxybenzyl)-4-(2-phenylethenyl)-1,2,3,6-tetrahydropyridine;
(E)-1-benzyl-4-[2-(indol-5-yl)ethenyl]-1,2,3,6-tetrahydropyridine; (E)-1-(4-chlorobenzyl)-4-[2-(indol-5-yl ethenyl]-1,2,3,6-tetrahydropyridine;
(E)-1-benzyl-4-[2-(2-chloropyridin-5-yl)ethenyl]-1,2,3,6-tetrahydropyridine;
(E)-1-benzyl-4-[2-(1-methylindol-5-yl)ethenyl]-1,2,3,6-tetrahydropyridine;
(E)-1-benzyl-4-[2-(3-fluoro-4-methoxy)phenylethenyl]-1,2,3,6-tetrahydropyridine;
(E)-1-(4-methoxybenzyl)-4-(2-phenylethenyl)-1,2,3,6-tetrahydropyridine;
(E)-1-(4-chlorobenzyl)-4-(2-phenylethenyl)-1,2,3,6-tetrahydropyridine;
(E)-1-(4-fluorobenzyl)-4-(2-phenylethenyl)-1,2,3,6-tetrahydropyridine;
(E)-1-(4-chlorobenzyl)-4-[2-(4-chlorophenyl)ethenyl]-1,2,3,6-tetrahydropyridine;
(E)-1-benzyl-4-[2-(3-methanesulphonylphenyl)ethenyl]-1,2,3,6-tetrahydropyridine;
(E)-1-(3,4-dichlorobenzyl)-4-(2-phenylethenyl)-1,2,3,6-tetrahydropyridine;
(E)-1-(4-methylbenzyl)-4-(2-phenylethenyl)-1,2,3,6-tetrahydropyridine;
(E)-1-(4-cyanobenzyl)-4-(2-phenylethenyl)-1,2,3,6-tetrahydropyridine;
(E)-1-(4-chlorobenzyl)-4-[2-(3-chlorophenyl)ethenyl]-1,2,3,6-tetrahydropyridine;
(E)-1-(4-nitrobenzyl)-4-(2-phenylethenyl)-1,2,3,6-tetrahydropyridine;
(E)-4-[2-(3-chlorophenyl)ethenyl]-1-(4-methylbenzyl)-1,2,3,6-tetrahydropyridine;
(E)-1-(4-iodobenzyl)-4-(2-phenylethenyl)-1,2,3,6-tetrahydropyridine;
(E)-4-(2-phenylethenyl)-1-(4-trifluoromethylbenzyl)-1,2,3,6-tetrahydropyridine;
(E)-4-[2-(4-chlorophenyl)ethenyl]-1-(4-methylbenzyl)-1,2,3,6-tetrahydropyridine;
(E)-4-[4-(2-phenylethenyl)-1,2,3,6-tetrahydropyridin-1-yl]methyl-imidazole;
and pharmaceutically acceptable salts thereof.

5. A pharmaceutical composition comprising a compound as claimed in claim 4 in association with a pharmaceutically acceptable carrier.

6. A method for the prevention and/or treatment of clinical conditions for which a dopamine receptor subtype ligand is indicated, which method comprises administering to a patient in need of such treatment an effective amount of a compound as claimed in claim 4.

* * * * *